United States Patent [19]
Crivello et al.

[11] Patent Number: 5,037,861
[45] Date of Patent: Aug. 6, 1991

[54] NOVEL HIGHLY REACTIVE SILICON-CONTAINING EPOXIDES

[75] Inventors: James V. Crivello, Clifton Park; Julia L. Lee, Schenectady, both of N.Y.

[73] Assignee: General Electric Company, Waterford, N.Y.

[21] Appl. No.: 391,761

[22] Filed: Aug. 9, 1989

[51] Int. Cl.⁵ .............................................. C08F 2/46
[52] U.S. Cl. .................................... 522/172; 528/15; 528/21; 528/23; 549/215
[58] Field of Search ................. 549/215; 522/172; 528/15, 21, 23

[56] References Cited
U.S. PATENT DOCUMENTS 3,219,624 11/1965 Cohen .................................. 549/215
3,455,877 7/1969 Plueddemann ..................... 549/215
4,083,856 4/1978 Mendicino .......................... 549/215
4,576,999 3/1986 Eckberg ............................. 549/215

Primary Examiner—Melvyn I. Marquis
Attorney, Agent, or Firm—Mark R. Warfield

[57] ABSTRACT

The present invention relates to epoxy function silicone monomers represented by the formula:

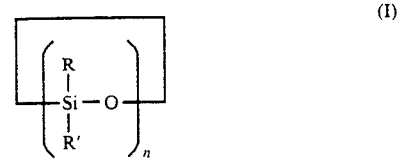

wherein
each R group is, independently, a monovalent substituted or unsubstituted $C_{1-12}$ alkyl, $C_{1-12}$ cycloalkyl, or phenyl radical;
each R' group is, independently, R, a monovalent $C_{2-12}$ alkyl radical, or a monovalent epoxy functional group having 2-10 carbon atoms with the proviso that at least one of the R' groups is epoxy functional; and n is from 3-10.

11 Claims, No Drawings

NOVEL HIGHLY REACTIVE SILICON-CONTAINING EPOXIDES

This invention relates to cyclic silicone monomers containing epoxy-functional groups which exhibit extraordinary reactivity in photoinitiated cationic polymerization.

BACKGROUND OF THE INVENTION

Epoxy resins have many desirable properties which make them attractive as coatings, adhesives, paper release agents, additives for printing inks, and for other applications. Included among these desirable properties are low viscosity, excellent clarity, high gloss, and high reactivity.

Additionally, epoxy resins have variable UV cure rates as measured by a PPG UV Processor. For example, 3,4-epoxycylcohexyl-methyl-3',4'-epoxycyclohexane carboxylate, a typical highly reactive cycloaliphatic epoxide obtained from Ciba-Gigy as "CY-179"; cures at a rate of 40 ft./min. under two 300 W UV lamps in the presence of 0.5 mole % (4-octyloxyphenyl)phenyliodonium hexafluoroantimonate.

E. P. Plueddemann and G. Fanger, *J. Am. Chem. Soc.*, vol. 81, p. 2632, 1959, describe the preparation of a number of silicon-containing epoxy monomers by hydrosilation of silicon hydrides and vinyl functional epoxides. Two of these epoxy monomers, which consist of short siloxane chains of two units terminated by cycloaliphatic epoxy groups, exhibit extraordinary reactivity when UV cured in the presence of diaryliodonium salts. The UV cure rates measured for these compounds are greater than 500 ft/min using a single 300 W UV lamp in the presence of 0.5 mole % (4-octyloxyphenyl)phenyliodonium hexafluoroantimonate.

It would be advantageous to develop different epoxy functional siloxane monomers based on a cyclic siloxane structure. Among the advantages are low initial viscosity, low toxicity, and high reactivity. Until now, however, cyclic epoxy-functional siloxanes have not been produced because side reactions caused premature crosslinking and the formation of gels.

U.S. Pat. Nos. 4,219,654 (Crivello); 4,026,705 (Crivello et al.); and 4,417,061 (Crivello) describe the use of diaryliodonium and trialylsulfonium salts as efficient photoinitiators in the cationic polymerization of epoxy resins and monomers. Included among the epoxy resins and monomers are polydimethylsiloxane resins having pendant and terminal glycidyl ether groups. The problem with resins which contain both pendant and terminal epoxy functional groups, however, is that, since they are polymeric, their viscosity is relatively high as compared to low molecular weight resins which contain only terminal epoxy functional groups. This limits their utility in coating and other applications where low viscosity compositions are required.

It is an object of this invention, therefore, to produce novel cyclic epoxy functional silicone monomers which have low initial viscosity yet are highly reactive in cationic photo-initiated polymerization reactions.

It is further an object of this invention to determine a method of producing cyclic epoxy functional silicone monomers which have low initial viscosity yet are highly reactive in cationic photoinitiated polymerization reactions.

Still further it is an object of this invention to produce an epoxy functional siloxane monomer that has low toxicity.

SUMMARY OF THE INVENTION

According to this invention there is provided an epoxy functional siloxane of the formula:

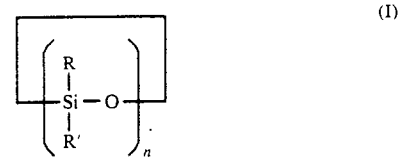

wherein
each R group is, independently, a monovalent substituted or unsubstituted $C_{1-12}$ alkyl, $C_{1-12}$ cycloalkyl, or phenyl radical;
each R' group is, independently, R, a monovalent $C_{2-12}$ alkyl radical, or a monovalent epoxy functional group having 2-10 carbon atoms with the proviso that at least one of the R' groups is epoxy functional; and n is from 3-10.

Also according to this invention, there is provided a method of making the epoxy functional siloxanes of formula (I) comprising the steps of:
1. Adding to a reactor a mixture comprising:
   a. a silicone hydride and
   b. an ethylenically unsaturated epoxide; and
2. Removing water and oxygen; and
3. Initiating a hydrosilation reaction between the components of the mixture.

There is further provided by this invention the cured product of formula (I) by photo and/or thermal polymerization.

DETAILED DESCRIPTION OF THE INVENTION

It is an object of this invention to provide a cyclic epoxy functional siloxane of the formula:

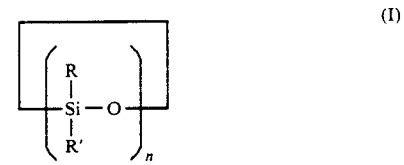

wherein
each R group is, independently, a monovalent substituted or unsubstituted $C_{1-12}$ alkyl, $C_{1-12}$ cycloalkyl, or phenyl radical;
each R' group is, independently, R, a monovalent $C_{2-12}$ alkyl radical, or a monovalent epoxy functional group having 2-10 carbon atoms with the proviso that at least one, and preferably, at least two, of the R' groups is epoxy functional;
and n is from 3-10.

Preferably, R is methyl, R' is methyl or a cycloaliphatic epoxy group, and n is 4. More preferably, R is methyl, R' is a cycloaliphatic epoxy group, and n is 4.

It is also contemplated that the hydrogen atoms on the R groups may be halogen substituted, preferably fluorine. Thus, one embodiment of this invention will have R defined as $C_{1-12}$ haloalkyl, preferably fluoroalkyl. More preferably, in the case of halo substitution, R would be defined as trifluoropropyl.

The physical properties of the final cured product may also be affected by the amount of crosslinking that may be done between the epoxy groups of the monomer of formula (I). As crosslinking "density" increases, the cured product increases in hardness and decreases in tensile strength and modulus. Thus, practitioners may be able to tailor the hardness, tensile, and modulus of the final product to their needs by adjusting the number of alkyl groups within the monomer. It is contemplated that from 0 to $(n-1)$ of the R' groups in formula (I) are $C_{1-12}$ alkyl, preferably methyl.

As stated above, one benefit of using the monomers of formula (I) is the relatively low viscosity which allows for thin film coating applications. Where R is methyl, R' is either methyl or cycloaliphatic epoxy, and n is 4 the viscosity is from about 100 to about 150 centistokes at 25° C. Where R is methyl, R' is cycloaliphatic epoxy, and n is 4 the viscosity is approximately 2900 centistokes at 25° C. Thus, monomers contemplated by this invention would fall within the range of from about 10 to 5000 centistokes at 25° C.

Another benefit obtained from using the monomers of this invention is the high reactivity that is obtained from the relatively low energy UV sources. Such data is included in the experimental portion of this application.

The R' groups on the cyclic epoxy functional siloxanes of formula (I) above may be R groups or may be obtained by hydrosilation of cyclic silicone hydrides with ethylenically unsaturated organic epoxides or with mixtures of ethylenically unsaturated organic epoxides and ethylenically unsaturated organic compounds. The ethylenically unsaturated species of the epoxides and/or epoxide/organic mixture react with the silicone hydride via addition reaction in the presence of a precious metal catalyst, such as platinum, to produce a siloxane with epoxy functionality. Such hydrosilation reactions are taught in U.S. Pat. No. 4,743,377 (Ohtsu et al.), herein incorporated by reference.

The cyclic silicone hydrides contemplated herein are well known and may be produced, for instance, by the hydrolysis and condensation of hydrolyzable organosilicon compounds, e.g. dichlorodimethylsilane and chlorohydrogendimethylsilane. Cyclic silicone hydrides may also be obtained by equilibrating polyorganosiloxanes and polyorganohydrogensiloxanes in the presence of strong acids. Such cyclic silicone hydrides are well known in the art and may be represented by the formula:

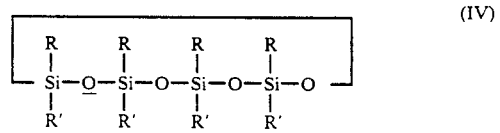
(II)

wherein
R and n are as previously defined,
and each R" group is, independently, R or hydrogen with the proviso that at least one of the R" groups is hydrogen.
Such cyclic silicone hydrides are disclosed in U.S. Pat. No. 4,743,377 (Ohtsu et al.), herein incorporated by reference.

The ethylenically unsaturated organic epoxides, which may react to form the epoxy-functional R' groups disclosed above, are any vinyl- or allyl-functional epoxides which will undergo addition reactions with SiH-functional groups. Preferably, the epoxides are vinyl functional cycloaliphatic epoxides. Most preferably, the vinyl functional epoxide is 3-vinyl-7-oxabicyclo[4.1.0]heptane and is represented by the following formula:

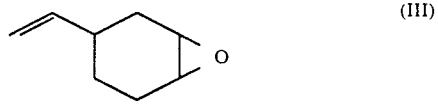
(III)

Additional ethylenically unsaturated epoxides which will react to form the R' groups above that have been found to be useful in this invention include 3-isopropenyl-6-methyl-7-oxabicyclo[4.1.0]-heptane (limonene monoxide); 3,4-epoxy-1-butene (butadiene monoxide); 5,6-epoxy-1-hexene; 7,8-epoxy-1-octene; 11,12-epoxy-1-dodecene; etc.

The ethylenically unsaturated organic compounds which also may be used to form the R' groups are any substituted or unsubstituted hydrocarbon of from 2 to 12 carbon atoms having one double bond per molecule. If there is more than one double bond, premature crosslinking between different molecules of the hydride will occur resulting in the formation of gels. It is preferable that the double bond be on the terminal group of the organic compound. The physical properties of the final, cured product may be varied by varying the chain length of the organic group. As chain length increases, hardness decreases, and tensile, elongation, and modulus increases.

The hydrosilation catalyst which may be used to effect the addition of the ethylenically unsaturated epoxide or epoxide/organic mixture may be any suitable precious metal catalyst, preferably platinum. Such catalysts are well known in the art. Preferred catalysts are taught by Lamoreaux in U.S. Pat. Nos. 3,917,432; 3,197,433; and 3,220,972; hereby incorporated by reference.

The monomer that is obtained as a result of the above-mentioned hydrosilation reaction, and as represented by formula (I), is a cyclic epoxy functional siloxane monomer. Preferably, the monomer is a tetra-functional siloxane with 1-4 epoxy-functional radicals bonded to silicon by Si-C bonds.

Such a monomer is represented by the formula:

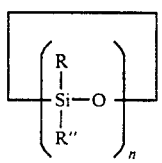
(IV)

wherein R and R' have been previously defined.

Initial attempts to prepare the epoxy functional monomers of this invention failed to due the presence of side reactions which led to the formation of the crosslinked gels. This was, nevertheless, overcome by excluding traces of water and oxygen from the reaction and is described in the experimental portion of this application.

The final cured product is achieved by adding to the epoxy-functional silicone of formula (I) a photosenitive onium salt and exposing the composition to sufficient UV light to initiate crosslinking. Such salts may be selected from the group consisting of diaryliodonium salts, triarylsulfonium salts, aryldiazonium salts, ferrocenium salts, diarylsulfoxonium salts, triarylsulfoxonium salts, dialkylphenacylsulfonium salts, dialkylhydroxyphenylsulfonium salts, phenacyltriarylphosphonium salts, and phenacyl salts of heterocyclic nitrogen-containing compounds. The effective amounts of such photosensitive onium salts ranges from about 0.1 to about 10 mole percent. Preferably, there is from about 1 to about 5 mole percent. Such photocatalysts are taught in U.S. Pat. Nos. 4,310,469 (Crivello); 4,175,972 (Crivello); 4,138,255 (Crivello); and 4,058,401 (Crivello) herein incorporated by reference.

In addition, photosensitizers may be employed which are useful in broadening the spectral sensitivity of the onium salts. Such photosensitive onium salts and photosensitizers are taught in U.S. Pat. Nos. 4,026,705 (Crivello et al.); 4,138,255 (Crivello); 4,219,654 (Crivello); and 4,417,061 (Crivello); herein incorporated by reference.

Further, using diaryliodonium salts together with copper cocatalysts and optionally using reducing agents, it has been shown possible to thermally initiate the polymerization of epoxy compounds. Such thermal polymerization is taught in U.S. Pat. Nos. 4,283,312 (Crivello); 4,239,725 (Crivello); and 4,225,691 (Crivello); herein incorporated by reference. Thus, an alternative process for obtaining the cured product of this invention comprises adding to the epoxy-functional siloxane of formula (I) a sufficient amount of diaryliodonium salt and copper cocatalyst and heating the composition.

The epoxy-functional silicone monomers described herein have a wide variety of potential uses. Among these may be mentioned coatings, encapsulants, molding compounds, matrix resins for fiber reinforced composites such as filament wound objects, pultrusions, and laminates. In addition, these epoxy monomers can be used in adhesives, elastomers, liquid injection molding, and in room temperature vulcanizable rubbers.

The process for making the epoxy-functional siloxanes of formula (I) comprises the steps of:
1. Adding to a reactor a mixture comprising:
a. a silicone hydride and;
b. an ethylenically unsaturated epoxide or mixture of ethylenically unsaturated epoxides and ethylenically unsaturated organic compounds; and
2. Removing water and oxygen; and
3. Initiating a hydrosilation reaction between the components of the mixture.

The preferred silicone hydrides and ethylenically unsaturated epoxides are disclosed in the passages above. In order to produce the cyclic epoxy-functional silicones of this invention it is important to remove the traces of water and oxygen from the reaction in order to prevent premature crosslinking and the subsequent formation of gels.

The hydrosilation reaction may be initiated by the introduction of a precious metal catalyst such as platinum. Such catalysts are well known in the art.

In order that those skilled in the art will be better able to practice the invention, the following examples are given by way of illustration and not be way of limitation.

EXAMPLE 1

Synthesis of Cyclic Tetrafunctional Epoxy Monomer

Into a 100 mL three necked round bottom flask equipped with a magnetic stirrer, a Dean Stark trap containing $CaH_2$, drying tube, nitrogen inlet, and reflux condenser were placed 52.1 g (0.42 mol) distilled 3-vinyl-7-oxabicyclo[4.,1.0]heptane and 24 g (0.1 mol) 2,4,6,8-tetramethylcyclotetrasiloxane ($D_4^H$) which had been dried over $CaH_2$ and then fractionally distilled under reduced pressure. There were also added 80 mL toluene and the reaction mixture refluxed through the trap for 2 h. The reaction mixture was cooled and 2 drops of the Lamoreaux catalyst was added. The reaction mixture was gradually warmed under a nitrogen blanket to 50°–55° C. and maintained at that temperature for 3 hours. After standing overnight, the IR of the reaction mixture showed the absence of a band at 2100 $cm^{-1}$. The solvent and excess epoxide starting material were removed under vacuum. There were obtained 52 g (87% yield) of cyclic tetrameric epoxide product.

The above tetrameric epoxide was combined with 0.5 mole % (4-octyloxyphenyl)phenyliodonium hexafluorophosphate and the mixture was spread as a 1 mil film onto a glass plate. The tack free UV cure rate was then determined in air using a Model QC 1202 UV Processor obtained from the RPC Equipment Company. This apparatus is equipped with two 12 inch medium pressure mercury arc lamps mounted perpendicular to the direction of travel of the conveyor. The lamps could be operated together or independently at 380 V and 6.8±0.8 amps. The lamps could also be operated at either high (300 W), medium (200 W) or low (120 W) power levels. It was found that the tack free cure rate using only one lamp at high power was greater than 500 ft/min. At low power using one lamp, the cure speed was 250 ft/min. In contrast, 3,4-epoxycyclohexylmethyl-3',4'-epoxycyclohexane carboxylate (a typical, high reactivity cycloaliphatic epoxy obtained from Ciba-Gigy as CY-179), required two lamps operating at 300 W to achieve a cure speed of 40 ft/min. The above experiment was performed using 0.5 mole % of (4-octyloxyphenyl)-phenyliodonium hexafluoroantimonate as a photoinitiator.

EXAMPLE 2

The Synthesis UV and Thermal Cure of a Cyclic Difunctional Epoxy-Silicone Monomer A mixture (20 g) containing the following proportions of cyclic oligomers: 85.3% $D_2^H D_2$, 7.5% $D_3^H D$ and 6.5% $D^H D_3$ (where D indicates a dimethylsiloxy group and $D^H$ indicates a methylhydrogensiloxy group; the subscript denotes the number of those groups in the ring) was placed into a 250 mL round bottom flask equipped with a magnetic stirrer, reflux condenser and nitrogen inlet. To this mixture was added 20 g (0.16 mol) 3-vinyl-7-oxabicyclo[4.1 0]heptane, 150 mL toluene. The reaction mixture was dried by azeotropic distillation through a $CaH_2$ trap for 1.5 hours, cooled and two drops of the Lamoreaux catalyst added. The temperature was raised to 50° C. for 1.5 hours; at that time the IR showed the absence of the 2100 $cm^{-1}$ band ascribed to the Si-H bond. The mixture was stirred overnight at room temperature and then the toluene and excess epoxy compound removed on a rotary evaporator. Lastly, the mixture of epoxy compounds was subjected to high vacuum stripping at 50° C.

The above mixture was combined with approximately 1% by weight of (4-octyloxyphenyl)phenyliodonium hexafluoroantimonate and then coated as a 1 mil film onto glass plates. The films were cured by irradiation with a GE H3T7 medium pressure mercury arc lamp at a distance of 6 inches. A tack-free time of less than 1 second was recorded. Using a PPG Processor, a cure rate of 500 ft/min was obtained using a single 300 W lamp and a photoinitiator concentration of 0.25 mol %.

There were mixed together 0.2 g (4-octyloxyphenyl)-phenyliodonium hexafluoroantimonate dissolved in 0.2 g propylene carbonate with 5 g of the above cyclic difunctional silicone epoxide. To this mixture was added 0.1 g stannous caproate and 10 mg copper naphthenate (Copper Chem-All from Mooney Chemicals, Inc.). Shortly after mixing, the color of the copper compound was discharged and within 40 seconds the mixture had hardened to a solid mass. This example demonstrates the use of cyclic silicone epoxy monomers in thermal (room temperature) curing systems.

EXAMPLE 3

Equilibration of Poly(dimethylhydrogensiloxane) with Poly(methylsiloxane) [Preparation of $D_2{}^H D_2$]

Into a 500 mL round bottom flask equipped with a magnetic stirrer, condenser, and nitrogen inlet were placed 18 g (0.3 mol segmer units) poly(dimethylsiloxane) fluid, 7.4 g (0.2 mol segmer units) poly(methylhydrogensiloxane), 100 mL hexane and 1.5 g trifluoromethanesulfonic acid. The reaction mixture was heated in an oil bath at 50° C. for two days. Gas chromatographic analysis showed complete redistribution of the linear polymers with the formation of a large fraction of mixed cyclics. The entire reaction mixture was filtered through a bed of MgO to remove the acid and then the n-hexane was removed on a rotary evaporator. Finally, the reaction mixture was fractionally distilled under reduced pressure. The fraction collected at 80°-82° C. consisted of a mixture of cyclic silicones including as major products $D_2{}^H D_2$, $D_4{}^H$ and $D^H D_3$.

EXAMPLE 4

The Preparation of a Trifunctional Cyclic Silicone Epoxy Monomer

Into a 100 mL round bottom flask was placed a mixture of 24.0 g (0.1 mol) 2,4,6,8-tetramethylcyclotetrasiloxane and one drop of the Lamoreaux catalyst. To the solution under a nitrogen blanket were added dropwise 8.4 g (0.1 mol) 1-hexene. The reaction mixture was heated to 50° C. for one hour after completion of the addition. Gas chromatography showed the absence of starting 1-hexene. The solution was distilled under vacuum and a fraction boiling at 44°-47° C. (10.2 g) was found to contain the desired 2-hexyl-2,4,6,8-tetramethylcyclotetrasiloxane. The $^1$H NMR spectrum is in agreement with the above structure.

To 10.2 g of the above cyclic siloxane there were added 12.4 g (0.1 mol) 3-vinyl-7-oxabicyclo[4.1.0]heptane in 80 mL toluene. The reaction mixture was azeotropically dried using a CaH$_2$ trap. The reaction mixture under a nitrogen blanket was cooled and one drop of the Lamoreaux catalyst was added. Then the reaction mixture was slowly warmed to 50° C. After 1.5 hours, the IR spectrum showed no absorption at 2100 cm$^{-1}$ indicating that the reaction had been completed. The toluene was removed on a rotary evaporator and then the last traces of solvent and starting epoxide were removed under high vacuum.

A. 1% solution of (4-octyloxyphenyl)phenyliodonium hexafloroantimonate in the above trifunctional epoxide was coated as a 1 mil film onto a glass plate. When irradiated using a GE H3T7 medium pressure mercury arc lamp at a distance of approximately 6 inches, the tackfree time was less than 1 second.

EXAMPLE 5

Preparation of Cyclic Siloxanes by Rearrangement of Linear Polydimethylsiloxanes To 40 g Type 5A molecular sieves (⅛ in. pellets) obtained from Alfa-Ventron Company, there were added 2 mL concentrated sulfuric acid. The sieves were placed in a three necked flask equipped with a distillation head, long condenser, receiver, flask, nitrogen capillary inlet and pressure equalizing addition funnel. After heating for 5 minutes at 200°-300° C., there were added dropwise by means of the addition funnel 56 g of a poly(methylhydrogensiloxane) fluid. Rapid distillation of the products occurred and were collected in the receiver. There were obtained a mixture of cyclic methylhydrogen siloxanes with major components $D_3{}^H$, $D_4{}^H$, $D_5{}^H$ and $D_6{}^H$.

The apparatus was reassembled and the catalyst again heated to 200°-300° C. There were slowly added an additional 51 g of the poly-(methylhydrogensiloxane) fluid. In the same manner, there were collected an additional 36 g of the above mixed cyclics.

EXAMPLE 6

Preparation of a Tetrafunctional Cyclic Epoxy Siloxane

A mixture of 18 g (0.075 equiv. Si-H) 2,4,6,8-tetramethylcyclotetrasiloxane and 31 g (0.32 mol) 1,2-epoxy-5-hexene in 110 mL toluene was placed in a 250 mL flask equipped with a reflux condenser, nitrogen inlet, and CaH$_2$ trap, and was refluxed for two hours. Then the solution was cooled and 2 drops of Lamoreaux catalyst was added. The reaction mixture was heated at 55° C. for 5 hours, then 70° C. for 1.5 hours. After cooling the reaction mixture, the toluene was removed on a rotary evaporator and then the excess epoxide was removed under high vacuum. There was obtained 41.1 g (86.7% yield) of the desired tetrafunctional epoxide.

When a 1% solution of (4-octyloxyphenyl)phenyliodonium hexafluoroantimonate in the above multifunctional epoxide was spread as a 1 mil film on a glass plate and irradiated using a GE H3T7 medium pressure mercury arc lamp, a tack-free time of 3 seconds was recorded.

What is claimed is:

1. A curable silicone composition comprising:
  1. a cyclic epoxy functional silicone monomer comprised of of siloxane units of the formula:

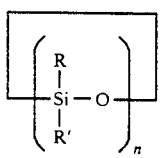

wherein each R group is, independently, a monovalent substituted or unsubstituted $C_{1-12}$ alkyl, $C_{1-12}$ cycloalkyl, or phenyl radical;

each $R^1$ group is, independently, R, a monovalent $C_{2-12}$ alkyl radical, or a monovalent epoxy functional group having 2-10 carbon atoms with the proviso that at least one of the $R^1$ groups is epoxy functional;

and n is from 3-10;

and 2. an onium salt photocatalyst selected from the group consisting of diaryliodonium salts, triarylsulfonium salts, aryldiazonium salts, ferrocenium salts, diarylsulfoxonium salts, triarylsulfoxonium salts, dialkylphenacylsulfonium salts, dialkylhydroxyphenylsulfonium salts, phenacyltriarylphosphonium salts, and phenacyl salts of heterocyclic nitrogen-containing compounds.

2. The curable silicone composition of claim 1 additionally comprising copper cocatalyst.

3. The curable silicone monomer of claim 1 wherein R is methyl, $R^1$ is methyl or cycloaliphatic epoxy functional group having 2-10 carbon atoms, and n is 4.

4. The curable silicone monomer of claim 3 wherein R is methyl, $R^1$ is cycloaliphatic epoxy functional group having 2-10 carbon atoms, and n is 4.

5. The curable silicone composition of claim 1 wherein R is a monovalent halogen substituted $C_{1-12}$ alkyl or a $C_{1-12}$ cycloalkyl radical.

6. The curable silicone composition of claim 5 wherein R is trifluoropropyl.

7. The curable silicone composition of claim 1 wherein the number of $C_{2-12}$ alkyl groups represented by $R^1$ is from 0 to (n−1), wherein n is from 3-10.

8. The curable silicone monomer of claim 1 wherein $R^1$ is cycloaliphatic epoxy functional group having 2-10 carbon atoms or ethyl.

9. The composition of claim 1 which is cured by exposure to UV radiation.

10. The composition of claim 2 which is cured by exposure to either UV radiation or heat or to a combination of UV radiation and heat.

11. The composition of claim 1 wherein at least two of the $R^1$ groups is epoxy functional.

* * * * *